United States Patent
Kornrumpf et al.

(10) Patent No.: US 6,415,169 B1
(45) Date of Patent: Jul. 2, 2002

(54) MULTIPLE ELECTRODE ASSEMBLY WITH EXTENDIBLE ELECTRODES AND METHODS OF FABRICATION AND APPLICATION

(75) Inventors: William Paul Kornrumpf, Schenectady, NY (US); Shankara Bonthu Reddy, Cedarburg, WI (US); David Anthony Lovejoy, Thiensville, WI (US); Donald Eugene Brodnick, Cedarburg, WI (US)

(73) Assignee: General Electric Company, Schenectady, NY (US)

( * ) Notice: Subject to any disclaimer, the term of this patent is extended or adjusted under 35 U.S.C. 154(b) by 67 days.

(21) Appl. No.: 09/583,405

(22) Filed: May 31, 2000

(51) Int. Cl.[7] .............................................. A61B 5/0408
(52) U.S. Cl. ........................ 600/382; 600/386; 600/391; 600/393
(58) Field of Search .................. 600/382, 386, 600/388–393, 396; 607/149, 152, 153

(56) References Cited

U.S. PATENT DOCUMENTS

| | | | | |
|---|---|---|---|---|
| 4,353,372 A | * | 10/1982 | Ayer | 600/393 |
| 4,583,549 A | * | 4/1986 | Manoli | 600/393 |
| 4,763,660 A | * | 8/1988 | Kroll et al. | 600/393 |
| 4,957,109 A | * | 9/1990 | Groeger et al. | 600/393 |
| 5,042,481 A | * | 8/1991 | Suzuki et al. | 600/393 |
| 5,341,806 A | * | 8/1994 | Gadsby et al. | 600/393 |
| 5,546,950 A | * | 8/1996 | Schoeckert et al. | 600/393 |
| 5,782,238 A | | 7/1998 | Beitler | |
| 5,916,159 A | | 6/1999 | Kelly et al. | |
| 6,055,448 A | * | 4/2000 | Anderson et al. | 600/393 |

* cited by examiner

Primary Examiner—Lee Cohen
(74) Attorney, Agent, or Firm—Ann M. Agosti; Jill M. Breedlove

(57) ABSTRACT

A flexible multiple electrode assembly includes at least one fixed electrode; at least one extendible electrode; and electrically conductive interconnections coupling the at least one fixed electrode and the at least one extendible electrode to a common connector. The at least one extendible electrode is adapted to be physically separable from the at least one fixed electrode while remaining electrically coupled to the common connector. In one embodiment, an array of fixed and extendible electrodes is configured for the acquisition of electrical pulses from a heart for transmission to an electrocardiograph (EKG or ECG) device.

16 Claims, 5 Drawing Sheets

MULTIPLE ELECTRODE ASSEMBLY WITH EXTENDIBLE ELECTRODES AND METHODS OF FABRICATION AND APPLICATION

BACKGROUND

The invention relates generally to electrodes and more particularly to multiple electrode assemblies for use in electrocardiograph (EKG or ECG) devices.

Electrocardiographic (EKG) devices are medical devices which record electrical impulses generated by a patient's heart and display the impulses on a monitor and/or record the impulses on paper or electronic media. EKG tracing typically involves positioning ten electrodes on the surface of the patient's body with each electrode corresponding to a particular area of the patient's heart. Generally six of the electrodes (V1–V6) are positioned in the rib cage area and the remaining four electrodes are respectively positioned in the area of the right arm (RA), left arm (LA), right leg (RL) and left leg (LL). Proper positioning of the electrodes is necessary to achieve a correct reading of the EKG. Accurately positioning and attaching the electrodes can be difficult and time consuming and requires a skilled technician or nurse.

Conventional electrodes are positioned with each electrode separately attached to an individual respective lead wire. The lead wires are connected to an electrocardiograph device by way of an interconnect cable. The lead wires have a tendency to become tangled with one another—thus making the attachment process more difficult.

A number of patents, such as Beitler, U.S. Pat. No. 5,782,238, and Kelly et al., U.S. Pat. No. 5,916,159, for example, have been directed to techniques for coupling the electrodes to a common connector. Beitler describes a flexible pad including multiple embedded electrodes (V1 to V6) grouped in plural sets of electrodes corresponding to particular body sizes and a switch to select the appropriate set with the pad being held in place by a weight. Kelly et al. describes an embodiment wherein several non-conductive sheets each have a single array of electrodes (V1 to V6) positioned thereon and coupled to a common connector such that most body sizes can be accommodated by having a few different sizes of sheets. Both Beitler and Kelly et al. appear to be limited to a multiple electrode array of chest electrodes V1 to V6.

BRIEF SUMMARY

It would be desirable to have a multiple electrode assembly that can more easily be applied to patients having different body sizes.

Briefly, in accordance with one embodiment of the present invention, a multiple electrode assembly comprises at least one fixed electrode; at least one extendible electrode; and electrically conductive interconnections coupling the at least one fixed electrode and the at least one extendible electrode to a common connector. The at least one extendible electrode is adapted to be physically separable from the at least one fixed electrode while remaining electrically coupled to the common connector.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description taken in conjunction with the accompanying drawings, where like numerals represent like components, in which:

DETAILED DESCRIPTION OF THE INVENTIONS

Figure 1:
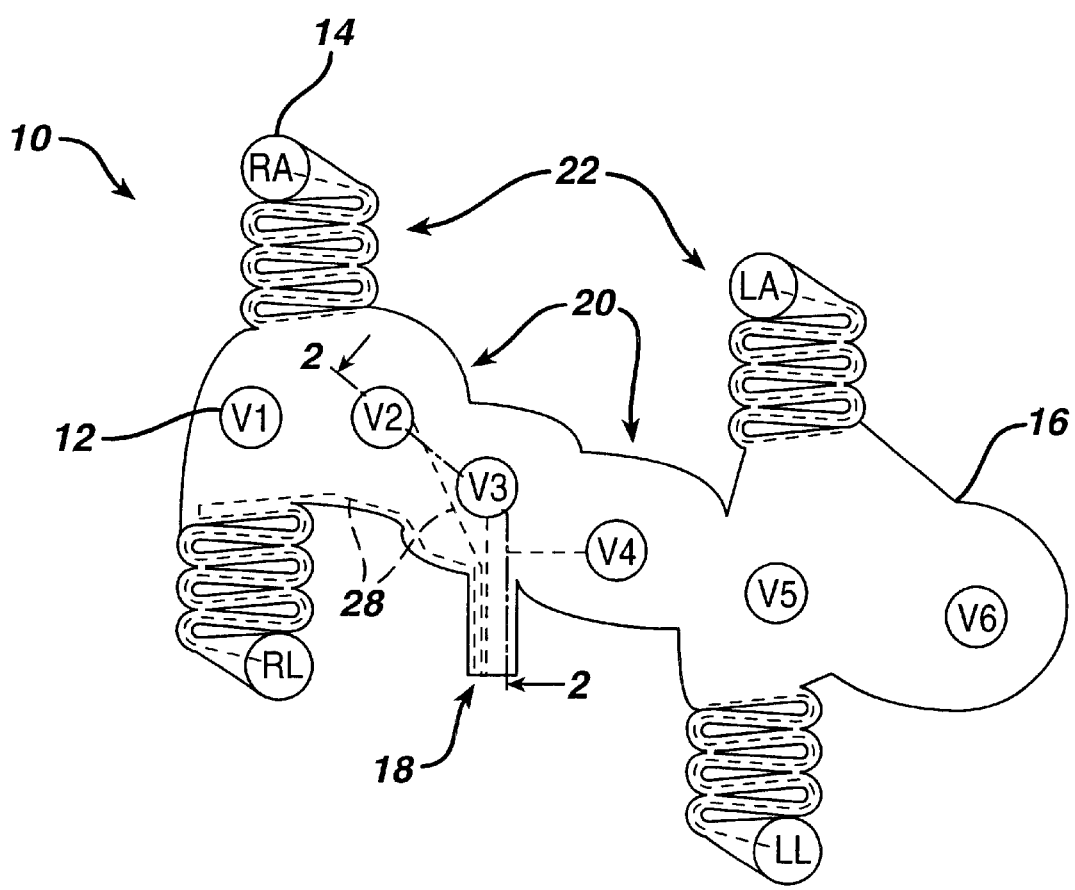
FIG. 1 is a top view of a multiple electrode assembly including extendible electrodes according to one embodiment of the present invention.

FIG. 1 is a top view of a multiple electrode assembly 10 including fixed electrodes 12 and extendible electrodes 14 according to one embodiment of the present invention. In this embodiment, the multiple electrode assembly comprises at least one fixed electrode 12 (shown for purposes of example as six fixed electrodes V1 to V6) and at least one extendible electrode 14 (shown for purposes of example as four extendible electrodes RA, LA, RL, LL) adapted to be physically separable from the at least one fixed electrode while remaining partially coupled to the at least one fixed electrode.

Non-conductive backing material 16 provides a surface to support both the at least one fixed electrode and the at least one extendible electrode. The backing material includes a fixed portion 20 which supports the at least one fixed electrode (as well as common connector 18) and an extendible portion 22 which supports the at least one extendible electrode. Electrically conductive interconnections 28 are supported by the backing material and couple the electrodes to a common connector 18. Although electrically conductive interconnections 28 are shown in FIG. 1 for the RL and V2–V4 electrodes for purposes of example, typically an electrically conductive interconnection will be present for each electrode.

FIGS. 2–6 are sectional side views of stages of a process useful for fabricating the multiple electrode assembly along the line 2—2 of FIG. 1. Although not shown in FIGS. 2–6, extendible electrodes 14 can be fabricated simultaneously with fixed electrodes 12 in a similar manner. In these embodiments, backing material 16 includes a first substrate 24, a flexible interconnect layer 26, and a second substrate 30 (shown in FIGS. 3–6).

Figure 2:
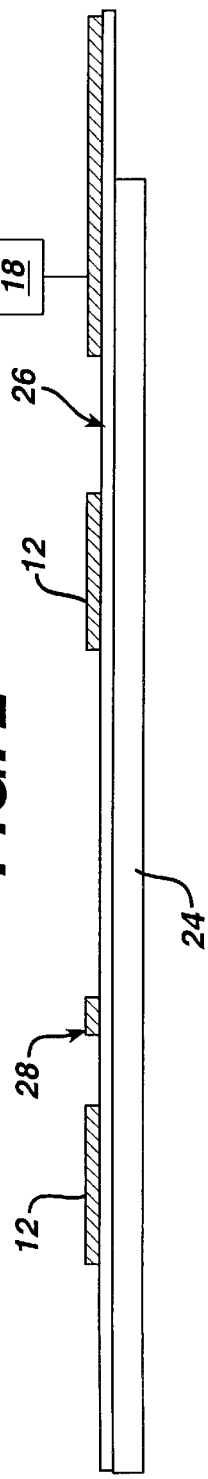
FIGS. 2–6 are sectional side views of stages of a process useful for fabricating the multiple electrode assembly of FIG. 1.

In FIG. 2, first substrate 24 comprises material which will be positioned away from the surface of a patient. In one embodiment, the first substrate comprises an insulating foam or a cloth material, for example. Overlying substrate 24 in FIG. 2 is flexible interconnect layer 26 that can be attached to substrate 24 by an adhesive (not shown), for example. In one embodiment, the flexible interconnect layer comprises polymer material. The flexible interconnect layer may optionally be pre-patterned. In an alternative embodiment, first substrate 24 is not used (that is, a flexible interconnect layer performs the interconnect and support functions of both flexible interconnect layer 26 and substrate 24).

Overlying or integrated within flexible interconnect layer 26 in FIG. 2 are electrodes 12 and electrically conductive interconnections 28. Although not shown in FIG. 2, electrodes 14 additionally overly or are integrated within flexible interconnect layer 26. Electrodes 12 and 14 and electrically conductive interconnections can be applied to flexible interconnect layer 26 either before or after the flexible interconnect layer is attached to first substrate 24. In one embodiment, for example, metallization is applied and patterned on the flexible interconnect layer to form the electrodes and interconnections, and then the flexible interconnect layer is attached to the first substrate by an adhesive (not shown) such as an acrylic adhesive, for example.

Appropriate materials for the electrodes and the interconnections include materials that are compatible with the device to which the common connector will be mated. Preferably the electrodes have a silver/silver chloride or carbon coating thereon that is compatible with common conductive adhesive gel materials 34 (shown in FIG. 4) that are used to couple the electrodes to skin. Although electrically conductive interconnections are shown on outer surfaces of flexible interconnect layer 26 for purposes of example, to conserve surface space the electrically conductive interconnections can alternatively be buried within flexible interconnect layer 26. In one embodiment, flexible interconnect layer 26 comprises multiple polymer layers and electrically conductive interconnection layers (not shown).

Figure 3:
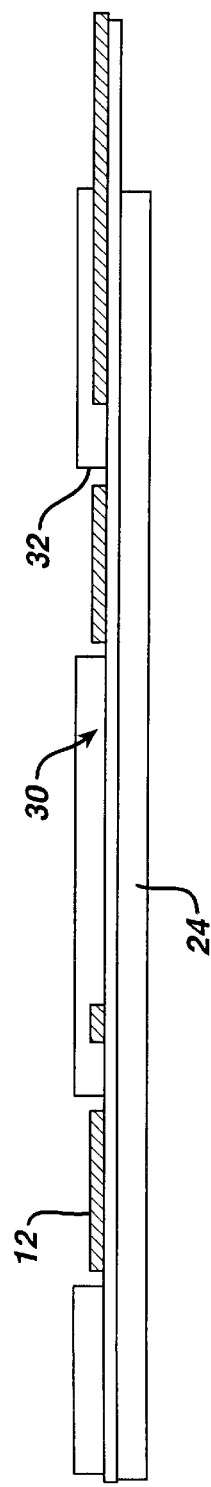

In FIG. 3 a second substrate 30 is shown over first substrate 24, flexible interconnect layer 26, and electrically conductive interconnections 28. Second substrate 30 comprises a material such as foam or cloth, for example, and can be attached to the first substrate and flexible interconnect layer 26 via an adhesive (not shown). Second substrate 30 has second substrate windows 32 which expose the at least one fixed electrode and the at least one extendible electrode. Second substrate windows 32 can be patterned either prior to or after the second substrate is attached to the electrode assembly.

Figure 4:
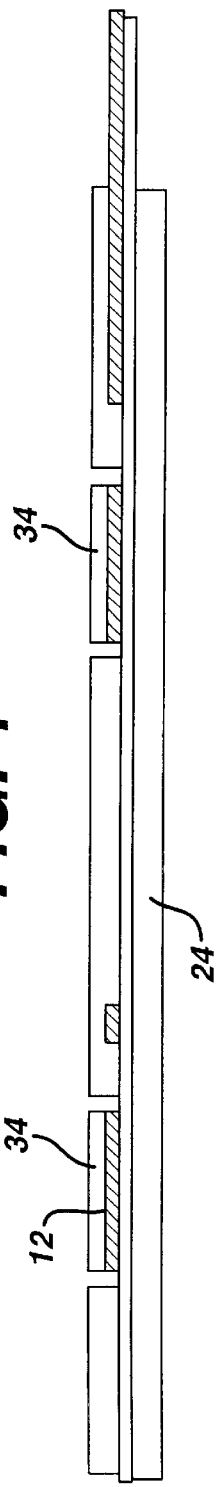

As shown in FIG. 4, skin adhesive gel material 34 is then applied to the surfaces of the electrodes. In one embodiment, the skin adhesive gel material comprises a hydrogel electrolyte having adhesive characteristics that allow the hydrogel electrolyte to both bond to the electrodes and provide good electrical contact with human skin.

Figure 5:
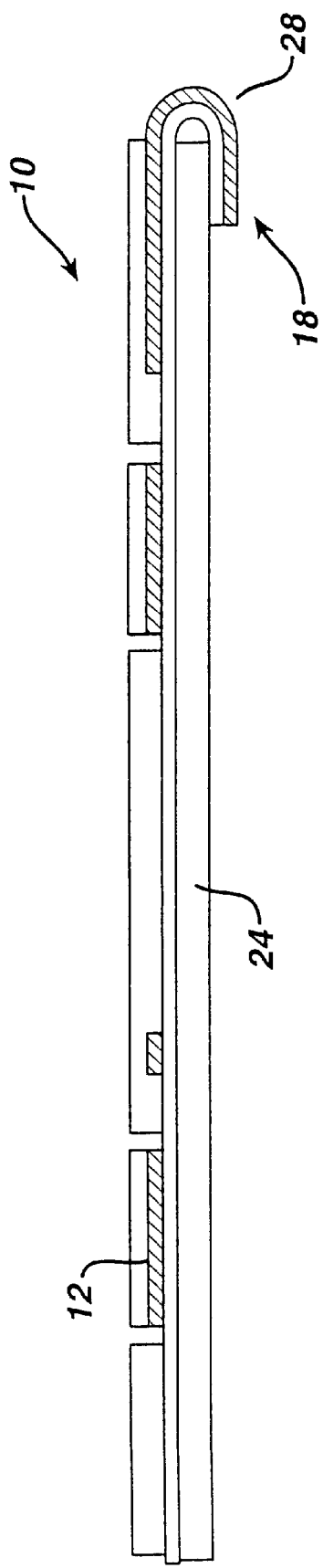
Figure 10:
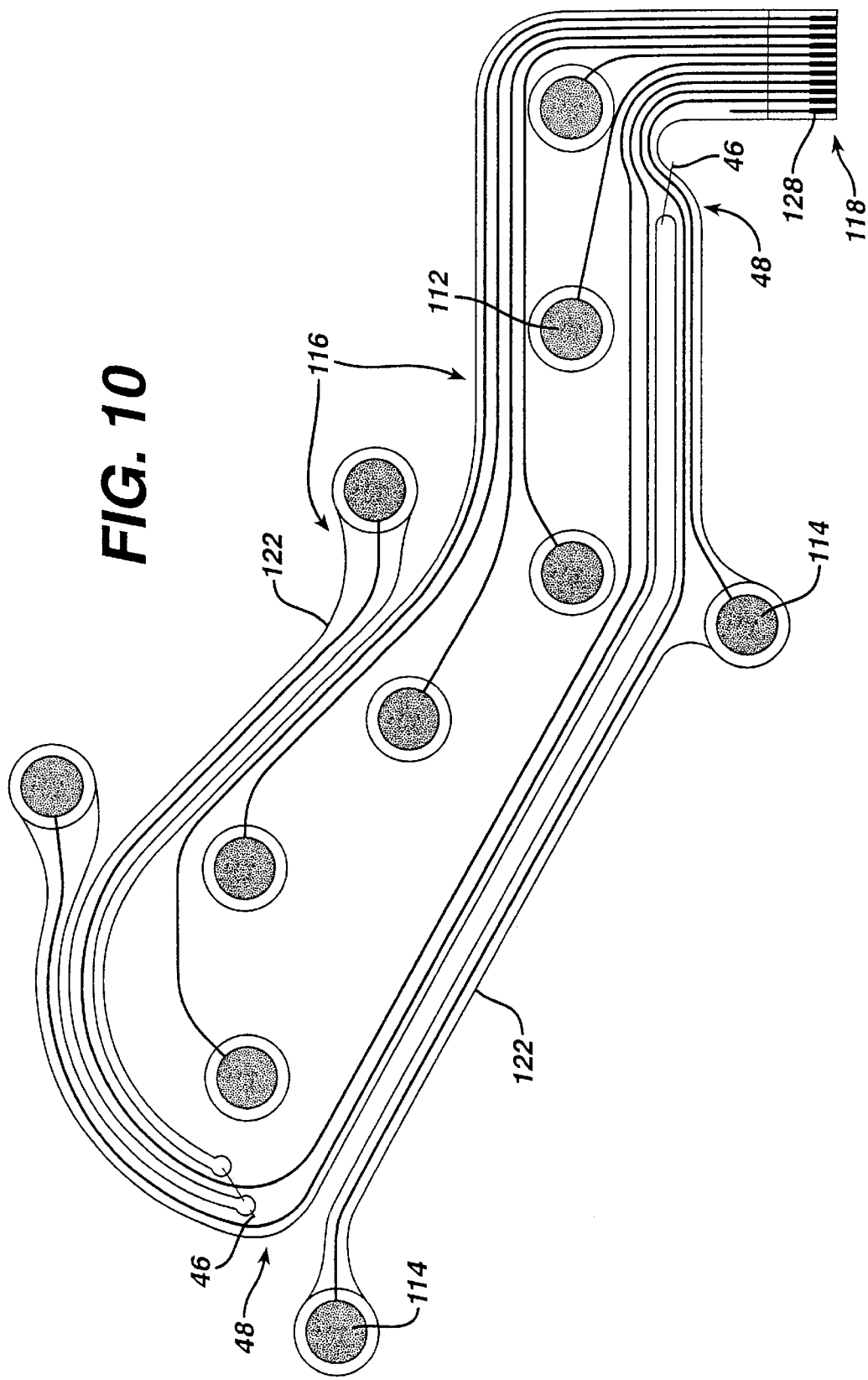
FIG. 10 is a top view of a multiple electrode assembly according to another embodiment of the present invention.

FIGS. 2–4 illustrate a straight common connector 18 that can accept crimp-type terminal contacts used with or without a connector housing. FIG. 5 illustrates the common connector folded over on itself. Straight or folded common connectors are typical of connector systems that have a pressure type connector system or a low insertion force type connector system that mates with the non-conductive substrates 24 and 30 and interconnection layer 26. Folding common connectors are particularly useful if the substrate and flexible interconnect layer materials are thin and require additional mechanical rigidity. In one embodiment, as shown in FIG. 5, electrically conductive interconnections 28 can then be used as the contacts of a connector which fits in a mating connector (not shown) common in the printed wiring board industry. As shown in the embodiment of FIG. 10, it can additionally help to have the electrically conductive interconnections 128 be patterned to be wider in the area of the connector 118.

Figure 6:
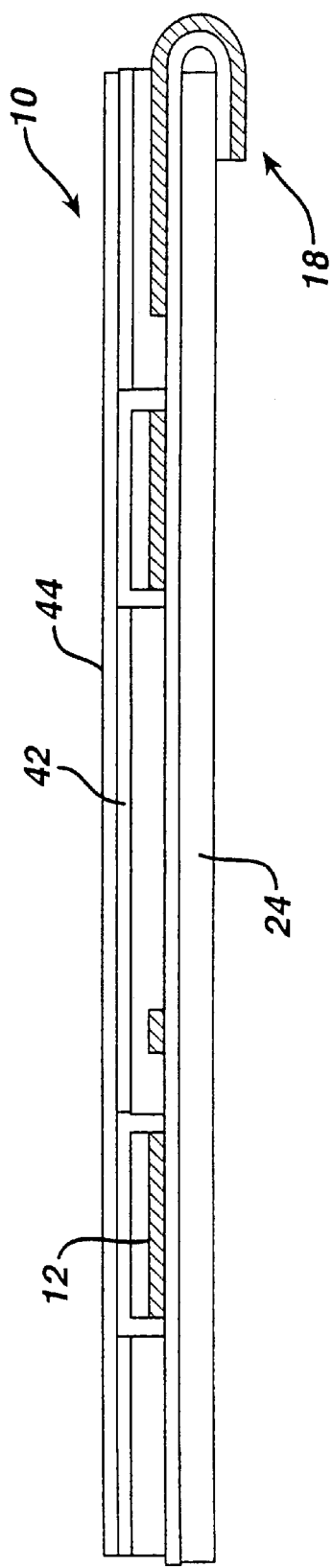

FIG. 6 illustrates an additional adhesive 42 that is non-conductive and appropriate for contact with skin and that can be present on portions of second substrate 30. A peelable liner 44 can cover the electrodes and second substrate 30 for protection of the surfaces and of adhesives 34 and 42.

Figure 9:
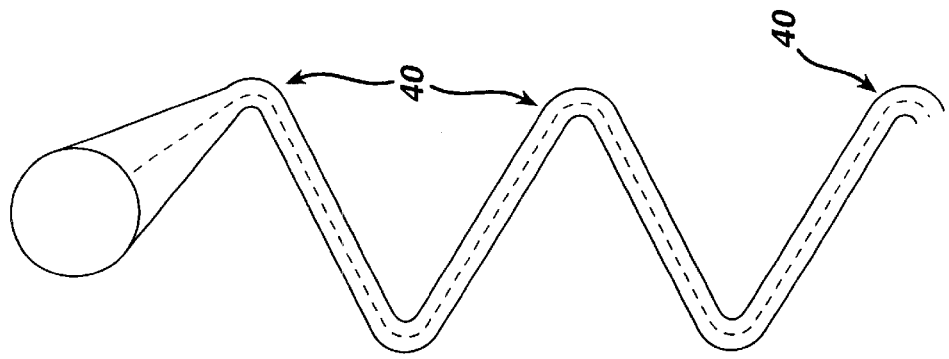
FIGS. 7–9 are top views illustrating various positions of an extendible electrode of the type shown in FIG. 1.
Figure 8:
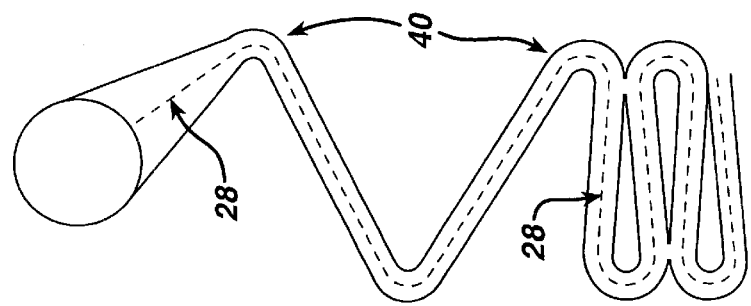
Figure 7:
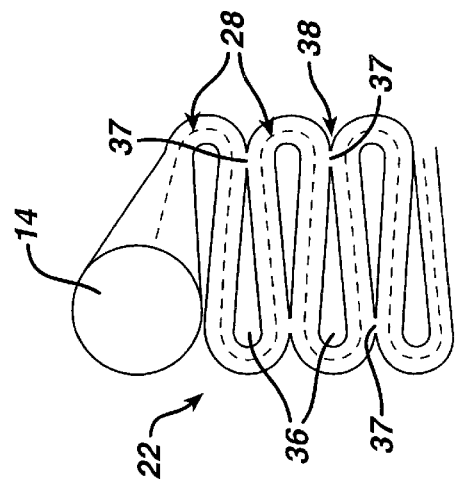

FIGS. 7–9 are top views illustrating various positions of an extendible electrode according to one embodiment of the present invention. The patterning of extensible portion 22 of backing material 16 (FIG. 1) shown in FIG. 7–9 is one of many designs that can be configured to provide an extendible electrode that remains attached to a fixed electrode array. One example of a technique for patterning backing material 16 includes mechanical punching, for example.

In the embodiments of FIGS. 7–9, extendible portion 22 of the backing material is patterned in a continuous serpentine shape with substrate openings 36 (having teardrop shapes, for example) and corresponding trimmed border areas 38 formed therein and temporary connective regions 37. Temporary connective regions 37 are adapted to be separable when the at least one extendible electrode is pulled away from the at least one fixed electrode. FIG. 7 shows the extendible portion in an original, unextended position prior to pulling, FIG. 8 shows the electrode partially pulled away with portions 40 of the electrically conductive interconnection 28 being separated, and FIG. 9 shows the electrode more fully extended. The extendible electrodes can be extended to a sufficient distance from the fixed electrodes to properly position them on the patient's body while being electrically coupled to common connector 18 through electrically conductive interconnections 28.

The embodiments of FIGS. 1–9 are for purposes of example only. For example, although FIG. 1 shows the V1–V6 electrodes as being fixed and the RA, LA, RL, and LL electrodes as being extendible, other arrangements can be used. For example, by creating appropriate shapes and electrically conductive interconnections between V2 and V3, V3–V6 can be extendible with respect to V1–V2 or vice versa and allow for patient torso size variations. For another example, LA and LL need not be positioned on opposing sides of V5. The exact arrangements and numbers and types of extendible electrodes will be limited only by spatial considerations in coupling each electrode to the common connector. Further, in addition to electrodes V1 to V6, fixed electrodes may include posteriorly-positioned electrodes V7 to V10 (not shown) and/or right-sided electrodes V3R–V6R (not shown).

FIG. 10 is a top view of a multiple electrode assembly according to another embodiment of the present invention wherein the extendible portions 122 of the backing material 116 are patterned to form hinges 48 which may include curved and/or linear shapes. FIG. 10 further illustrates an embodiment wherein an extendible portion of the backing material comprises a plurality of extendible portions with at least one of the plurality of extendible portions supporting at least two extendible electrodes 114.

In one embodiment, liner 44 (shown in FIG. 6) includes fixed and extendible liner portions to protect the extendible electrodes while the fixed electrodes 112 to are attached to skin. Each respective extendible liner portion can conveniently be pulled away prior attachment of its respective extendible electrode or electrodes 114. For purposes of example, lines 46 of FIG. 10 represent examples of areas of the backing material 116 over which the divisions between fixed and extendible liner portions can be made.

While only certain features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. A multiple electrode assembly comprising:
   at least one fixed electrode;
   at least one extendible electrode; and electrically conductive interconnections coupling the at least one fixed electrode to and the at least one extendible electrode to a common connector, the at least one extendible electrode adapted to be physically separable from the at least one fixed electrode while remaining electrically coupled to the common connector; and backing material supporting the electrically conductive interconnections and including a fixed portion supporting the at least one fixed electrode and an extendible portion supporting the at least one extendible electrode, wherein the extendible portion of the backing material is patterned in a continuous serpentine shape with openings and corresponding trimmed border areas formed therein and temporary connective regions, the temporary connective regions adapted to be separable when the at least one extendible electrode is pulled away from the at least one fixed electrode.

2. The assembly of claim 1 wherein the backing material includes a flexible interconnect layer supporting the at least one fixed electrode, the at least one extendible electrode, the electrically conductive interconnections and the common connector.

3. The assembly of claim 2 wherein the backing material further includes:

a first substrate supporting the flexible interconnect layer, and a second substrate over the first substrate and the flexible interconnect layer and having second substrate windows exposing the at least one fixed electrode and the at least one extendible electrode.

4. The assembly of claim 3 wherein the first substrate includes a foam or cloth material, the second substrate includes a foam or cloth material, and the flexible interconnect layer includes a polymer material.

5. The assembly of claim 4 wherein the extendible portion of the backing material is patterned to form a hinge.

6. The assembly of claim 5 wherein the extendible portion of the backing material comprises a plurality of extendible portions with at least one of the plurality of extendible portions supporting at least two extendible electrodes.

7. A multiple electrode assembly for electrocardiograph devices comprising:

an array of fixed electrodes;

a plurality of extendible electrodes;

electrically conductive interconnections;

a flexible interconnect layer supporting the fixed electrodes, the extendible electrodes, and the electrically conductive interconnections;

a first substrate supporting the flexible interconnect layer; and a second substrate over the first substrate and the flexible interconnect layer and having second substrate windows exposing the fixed electrodes and the extendible electrodes, the first and second substrates and the flexible interconnect layer collectively comprising backing material with a fixed portion of the backing material supporting the fixed electrodes and an extendible portion of the backing material supporting the extendible electrodes, the extendible electrodes being physically coupled to the fixed portion of the backing material by the extendible portion of the backing material and electrically accessible from the fixed portion of the backing material by the electrically conductive interconnections and the extendible portion of the backing material being patterned in a continuous serpentine shape with first and second substrate openings and corresponding trimmed border areas formed therein and temporary connective regions, the temporary connective regions adapted to be separable when the extendible electrodes are pulled away from the fixed electrodes.

8. The assembly of claim 7 wherein the fixed and extendible electrodes include silver/silver chloride or carbon.

9. The assembly of claim 7 further including electrically conductive skin adhesive gel material on the surfaces of the fixed and extendible electrodes.

10. The assembly of claim 9 further including electrically non-conductive skin adhesive on at least a portion of the surfaces of the second substrate.

11. The assembly of claim 10 further including a liner for protecting the electrically conductive skin adhesive gel material and the electrically non-conductive skin adhesive.

12. The assembly of claim 11 wherein the liner includes fixed and extendible liner portions.

13. A method of fabricating a multiple electrode assembly comprising:

providing backing material;

applying at least one fixed electrode to a fixed portion of the backing material;

applying at least one extendible electrode to an extendible portion of the backing material;

providing electrically conductive interconnections, the electrically conductive interconnections being supported by the backing material for coupling the at least one fixed electrode and the at least one extendible electrode to a common connector, wherein applying the at least one extendible electrode comprises applying the at least one extendible electrode in a manner so that the at least one extendible electrode is physically separable from the at least one fixed electrode while remaining electrically coupled to the common connector, wherein providing the backing material further includes patterning the backing material in a continuous serpentine shape with openings and corresponding trimmed border areas formed therein and temporary connective regions, the temporary connective regions adapted to be separable when the at least one extendible electrode is pulled away from the at least one fixed electrode.

14. The method of claim 13 wherein providing the backing material includes:

providing a first substrate, the first substrate supporting the at least one fixed electrode, the at least one extendible electrode, and the electrically conductive interconnections, and applying a second substrate over the first substrate and the electrically conductive interconnections and having second substrate windows exposing the at least one fixed electrode and the at least one extendible electrode.

15. The method of claim 14 wherein providing the backing material further includes providing a flexible interconnect layer supporting the at least one fixed electrode, the at least one extendible electrode, and the electrically conductive interconnections and situated between the first and second substrates.

16. The method of claim 15 wherein providing the backing material further includes patterning the extendible portion of the backing material to form hinges.

* * * * *